United States Patent [19]
Landis

[11] Patent Number: 5,490,841
[45] Date of Patent: Feb. 13, 1996

[54] SAFETY SHEATH DEVICE

[76] Inventor: Robert M. Landis, 1130 Puddingstone Rd., Mountainside, N.J. 07092

[21] Appl. No.: 282,608

[22] Filed: Jul. 29, 1994

[51] Int. Cl.$^6$ .................................................. A61M 5/00
[52] U.S. Cl. .......................... 604/110; 604/192; 604/263; 128/919
[58] Field of Search ..................................... 604/192, 187, 604/263, 198; 128/919

[56] References Cited

U.S. PATENT DOCUMENTS

| | | | |
|---|---|---|---|
| 2,854,976 | 10/1958 | Heydrich . | |
| 2,953,243 | 9/1960 | Roehr . | |
| 3,021,942 | 2/1962 | Hamilton . | |
| 3,323,523 | 6/1967 | Scislowicz . | |
| 3,324,853 | 6/1967 | Czorny . | |
| 3,537,452 | 11/1970 | Wilks . | |
| 3,610,240 | 10/1971 | Harautuneian . | |
| 3,658,061 | 4/1972 | Hall . | |
| 3,890,971 | 6/1975 | Leeson . | |
| 3,904,033 | 9/1975 | Haerr . | |
| 3,934,722 | 1/1976 | Goldberg . | |
| 4,139,009 | 2/1979 | Alvarez . | |
| 4,592,744 | 6/1986 | Jagger . | |
| 4,634,428 | 1/1987 | Cuu . | |
| 4,643,722 | 2/1987 | Smith . | |
| 4,659,330 | 4/1987 | Nelson . | |
| 4,664,259 | 5/1987 | Landis . | |
| 4,664,654 | 5/1987 | Strauss . | |
| 4,681,567 | 7/1987 | Masters . | |
| 4,723,943 | 2/1988 | Spencer . | |
| 4,735,618 | 4/1988 | Hagen . | |
| 4,747,836 | 5/1988 | Luther . | |
| 4,781,697 | 11/1988 | Slaughter . | |
| 4,790,828 | 12/1988 | Dombrowski . | |
| 4,795,443 | 1/1989 | Permenter . | |
| 4,804,372 | 2/1989 | Laico . | |
| 4,820,277 | 4/1989 | Norelli . | |
| 4,826,490 | 5/1989 | Byrne . | |
| 4,838,871 | 6/1989 | Luther . | |
| 4,863,434 | 9/1989 | Bayless . | |
| 4,867,746 | 9/1989 | Dufresne . | |
| 4,872,552 | 10/1989 | Unger . | |
| 4,883,469 | 11/1989 | Glazier . | |
| 4,886,503 | 12/1989 | Miller . | |
| 4,888,001 | 12/1989 | Schoenberg . | |
| 4,892,521 | 1/1990 | Laico . | |
| 4,944,397 | 7/1990 | Miller . | |
| 4,950,242 | 8/1990 | Alvarez . | |
| 4,976,699 | 12/1990 | Gold .......................................... | 604/192 |
| 4,982,842 | 1/1991 | Hollister . | |
| 5,139,489 | 8/1992 | Hollister . | |
| 5,154,285 | 10/1992 | Hollister . | |
| 5,188,611 | 2/1993 | Orgain . | |
| 5,232,454 | 8/1993 | Hollister . | |
| 5,232,455 | 8/1993 | Hollister . | |

FOREIGN PATENT DOCUMENTS

| 1233302 | 5/1971 | United Kingdom . |
|---|---|---|
| 8707162 | 12/1987 | WIPO . |
| 9109637 | 7/1991 | WIPO . |
| 9109638 | 7/1991 | WIPO . |
| 9109639 | 7/1991 | WIPO . |
| 9312991 | 7/1993 | WIPO . |

OTHER PUBLICATIONS

Concord/Portex "Needle Protection Device", 1991.

Primary Examiner—John D. Yasko

[57] ABSTRACT

A needle protection device is disclosed having an elongate housing with a longitudinal needle entrance portion defined between two housing side walls. At least one hinged door member is provided extending across the entrance portion to enclose the needle within the housing. In one embodiment the housing has a trap door attached by a resilient living hinge to one side wall and extending across the entrance portion to engage a door stop on the opposite side wall, so that the door is able to rotate about the hinge toward the first side wall to allow the needle to enter the housing, but is limited by the door stop in the degree of rotation away from the first side wall, thereby preventing a needle within the housing from exiting through the entrance portion. In alternative embodiments the door may extend less than the entire length of the housing and/or a needle engaging member, such as a needle engaging hook, may be provided to engage and retain the needle within the housing.

30 Claims, 9 Drawing Sheets

SAFETY SHEATH DEVICE

TECHNICAL FIELD

The present disclosure relates to an improved safety sheath device for surgical sharps and, more particularly, to a sheath device for a cannula type needlewhich may be actuated using a one-handed technique to enclose the needle without spray back of fluid or particulate bodily matter.

BACKGROUND

Considerable effort has been directed to reducing the transmission of disease, e.g., infections or viruses, which may result from the use of medical equipment, particularly surgical needles used with syringes and related equipment. Medical personnel routinely must administer surgical needles to patients, such as to give injections, and must dispose of the contaminated needle in a safe and effective manner. Containers for receiving the needle and syringe are well known and in use, but these do not address potential exposure of health care workers or other patients or personnel to contaminated needles or the consequent possibility of disease transmission during the period after removal of the needle from the patient but prior to depositing the needle and/or syringe into the disposal container. Because millions of injections and similar procedures are performed each year, any protective device intended to address this problem must not only be safe and effective, but also cost efficient. Devices have been proposed for protecting medical personnel and others after the needle has been removed from the patient and prior to depositing the needle in a disposal container. For example, Landis U.S. Pat. No. 4,664,259 discloses a housing hingedly attached to the needle hub. The Landis housing has a longitudinal slot to allow passage of the needle into the housing and a needle engaging hook member integral with the housing for engaging the needle and preventing the housing from being rotated to expose the used needle after the needle has entered the housing and engaged the hook member. Advantageously, the Landis housing may be rotated to the closed position in a one-handed motion. That is, the user holds the syringe and places the housing against a surface. By exerting pressure on the syringe the housing is biased into the closed position in alignment with and enclosing the needle without involving the user's other hand. Molding considerations indicate that the Landis hook member for engaging the needle may best be molded with the housing in the open position so that the needle retaining hook member may be accessed during molding both through the longitudinal slot as well as through an aperture in the rear wall of the housing opposite the slot. This is important since ease of molding contributes to the cost efficiency of the device. The Landis housing structure has been incorporated into NEEDLE PRO needle protection devices available from Concord/Portex, Keene New Hampshire, a Smiths Industries Company.

In the Landis and Concord/Portex structures the longitudinal slot for reception of the contaminated needle remains open as the needle passes through the slot and engages the hook member. As the needle passes the tip of the hook member the needle and/or hook member flex and thereafter resiliently snap into place after the needle passes the hook tip so that the needle is positioned behind the hook tip. Because the longitudinal slot is open at all relevant times during this closing motion, including when the needle snaps past the hook, it is possible that bodily fluids or tissue particles may become airborne and travel back out of the open slot toward the user. Indeed, the preferred one-handed technique for moving the housing from the open position to the closed position involves biasing the housing against a surface with the open longitudinal slot facing the user, so any fluid droplets or particulate matter exiting the slot after the needle snaps back against the hook after passing the hook tip necessarily are directed toward the user.

Thus, despite the significant advantages of the Landis housing structure there remains a need for a safety sheath device which not only securely covers a used needle in a one-handed motion but which also prevents exposure to contaminated bodily fluids or tissue particles released from the needle during closure of the housing about the needle.

SUMMARY OF THE INVENTION

The safety sheath device generally consists of an elongated housing having a base portion operatively connected to one end of a surgical sharp. By way of example, one end of the elongated housing is hingedly connected to the base of a surgical sharp such as a surgical needle, or to a structure operatively connected to the base of a surgical needle. The elongated housing has a substantially open base, an enclosed central region and a longitudinal entrance portion for permitting the surgical sharp to enter the housing as the housing is rotated about the flexible housing hinge into alignment with the surgical sharp. The longitudinal entrance portion permits the surgical sharp to enter the housing as the housing is rotated into alignment with the surgical sharp. Structure is provided to prevent the surgical sharp from exiting the housing in the event an attempt is made to rotate the housing out of alignment with the enclosed surgical sharp and the base, and to prevent fluid droplets or particulates from being propelled out of the slot toward the user.

In the preferred embodiment the longitudinal entrance portion is covered by a trap door extending a length of the housing entrance portion. Preferably, the length of the trap door is equal to at least the length of the surgical sharp to be enclosed. Most preferably, the trap door extends the entire length of the housing entrance slot. One side of the trap door is hingedly attached to the housing, and preferably is integrally molded as part of the housing so that the trap door is biased to close the housing entrance slot but is sufficiently resiliently attached to a housing wall to flex and allow the surgical sharp to enter the housing through the trap door. After the surgical sharp has passed the trap door, the trap door returns to an original position extending across the housing entrance portion. In one embodiment the free, unattached end of the trap door extends adjacent a door stop molded into the opposite wall of the longitudinal housing to prevent the needle from exiting the housing. In other embodiments, a needle-engaging hook member secures the needle in the housing, with the trap door preventing particles or droplets from exiting the housing.

The housing may be operatively associated with one end of a surgical sharp in any suitable manner. By way of example, the end of the housing hinge not attached to the housing may be frictional or matingly engaged with the hub of a hypodermic needle. Thus, a base portion connected to the housing hinge may be configured to include a female luer type fitting for receiving a hypodermic needle hub, and an opposing male luer type fitting to be received by a hypodermic syringe. It is further contemplated that the base portion could be attached or formed directly as part of a hypodermic syringe or as part of any other surgical device involving use of a cannula needle, such as a vacutainer for taking blood samples. As will be appreciated, other configurations may also be useful. The only requirement is that the the housing hinge be attached to or part of a device from which the needle or other surgical sharp extends. Preferably, the housing hinge biases the housing away from the needle.

In use, as the housing is rotated about the housing hinge to overcome the bias force of the housing hinge and into alignment with the surgical sharp the free end of the trap door moves away from the door stop toward the central interior of the housing as the door hinge flexes under pressure of the surgical needle against the trap door. After the needle has passed the trap door and is within the housing the trap door resiliently returns toward the door stop on the opposite wall such that the free end of the trap door is adjacent the door stop. Thereafter, if an attempt is made to rotate the housing out of alignment with the base the needle engages the inside surface of the trap door and urges the door outward. As the door moves outward, however, the free end of the trap door abuts the door stop to limit outward movement of the trap door. Thus, the trap door is closed and the surgical sharp is prevented from exiting the housing. In one-alternative embodiment a pair of trap doors are provided, and in further embodiments a needle-engaging hook may also be provided within the housing.

The safety sheath has numerous advantages. The device provides safe needle enclosure with a one-handed technique. Thus, with the device in the open position, i.e., with the housing out of alignment with the needle, the user places the rear of the housing away from the housing entrance slot against a surface, such as a table surface, to urge the housing to overcome the bias of the housing hinge and rotate about the housing hinge into alignment with the needle to enclose the needle. As the needle enters the housing the trap door opens and then closes to enclose the needle within the housing. Because the trap door substantially if not completely covers the needle entrance slot facing the user, the possibility of infectious droplets or particles being flung back through the entrance opening toward the user or any other person is substantially reduced. In the preferred embodiment no needle engaging hook member is required so relatively simple molds may be used. The safety sheath device is readily and inexpensively molded and provides convenient, effective one-handed needle enclosure without spray back of infectious droplets or particles. It is also contemplated that the safety sheath device could further include a hook type needle engaging member, if desired, for added security to ensure that the housing is securely locked over the surgical sharp.

These and other advantages are obtained by the safety sheath device as more fully described and claimed below. The safety sheath device may find application to the covering of any surgical sharp. For convenience, however, the present application describes the safety sheath device in the context of covering a cannula type surgical needle. It will be understood that such description is not intended to limit the scope or application of the device as described and claimed.

BRIEF DESCRIPTION OF THE DRAWINGS

The attached drawings form a part of the present application and, together with the following detailed disclosure, show various features of the preferred embodiments. Briefly, the drawings may be described as follows.

DETAILED DESCRIPTION OF THE PREFERRED EMBODIMENTS

Figure 1:
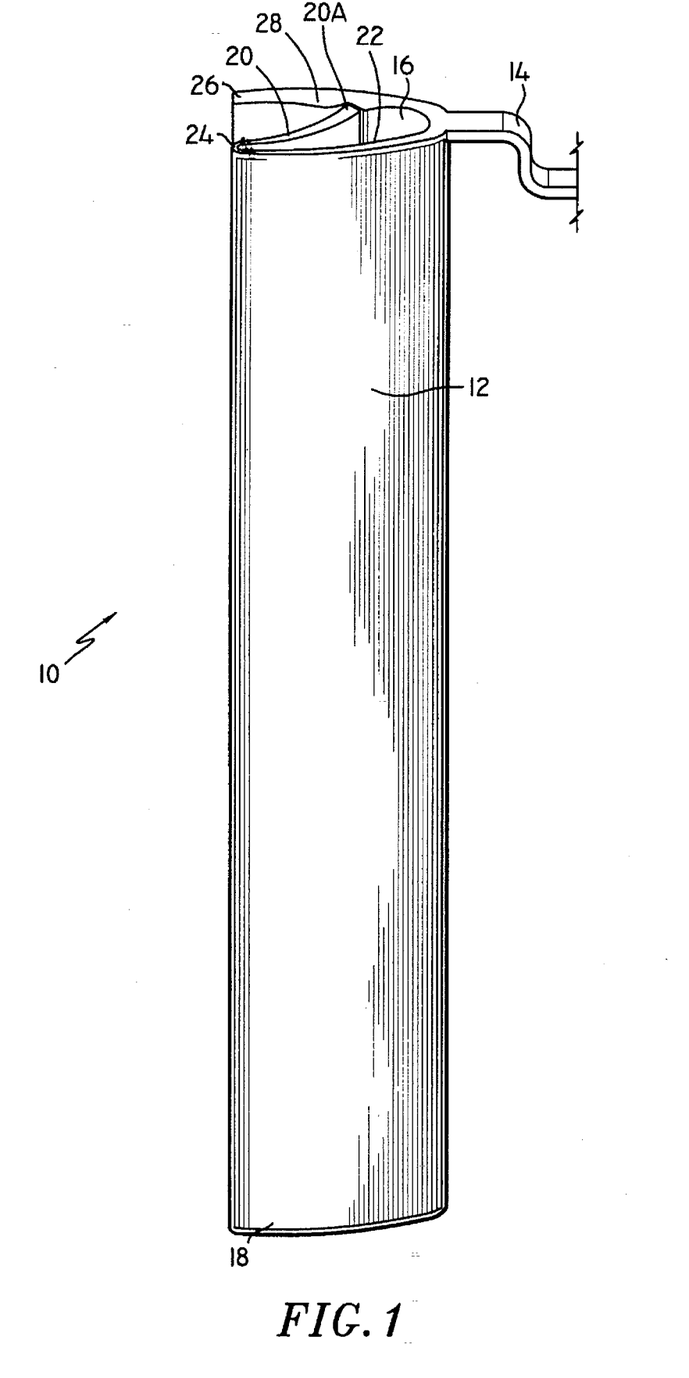
FIG. 1 is a perspective view of a safety needle sheath.

Referring to the drawings, particularly FIG. 1, a safety needle sheath device 10 generally consists of an elongated sheath or housing 12 connected at a proximal end thereof to a flexible housing hinge 14. Housing hinge 14 is operatively associated with the base of an elongated surgical sharp, such as a hypodermic needle. Several modes of operatively associating housing hinge 14 with the base of a needle are described in detail herein. For the purposes of the present disclosure, however, all that is important is that the housing hinge be or become attached to the base of the surgical sharp or needle to be covered, or to a structure which becomes attached to the base of such a surgical sharp.

Figure 2:
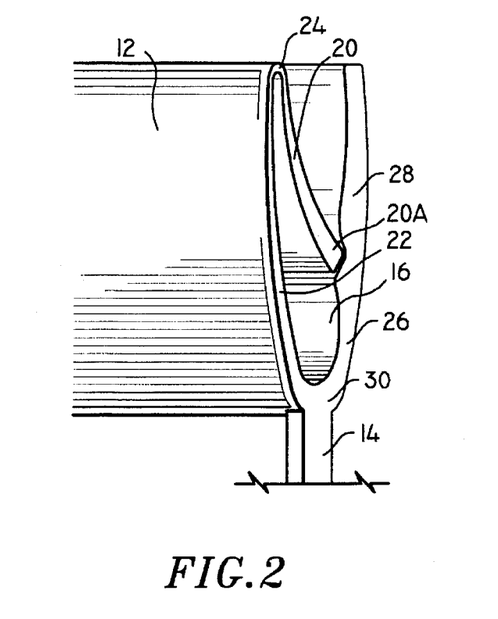
FIG. 2 is a partial perspective view of the proximal end of the sheath of FIG. 1.

Elongated sheath 12 has a substantially open proximal end 16 at the housing end attached to resiliently flexible hinge 14. As shown in FIGS. 1 and 2, sheath 12 has a trap door member 20 extending substantially or entirely along the longitudinal length of the side of the sheath opposite the side of the sheath attached to hinge 14. Trap door 20 is attached to a first sheath side wall 22 by a flexible door hinge 24, and extends from hinge 24 across the open elongated entrance portion of the sheath to a second, opposite sheath side wall 26. Second sheath side wall 26 preferably includes a door stop 28 which engages the free end 20A of door 20 to limit rotation of door 20 about hinge 24 in a direction away from first sheath wall 22. Thus, door 20 is able to rotate about door hinge 24 toward first sheath side wall 22, but rotation of trap door 20 away from first sheath side wall 22 is limited by engagement of the trap door free end 20A with door stop 28. Trap door hinge 24 biases door 20 away from first side wall 22 toward second side wall 26. As will be explained in greater detail below, a surgical sharp such as a surgical needle passes into the safety sheath by pushing against the trap door, causing the trap door to rotate about hinge 24 toward first side wall 22 to allow the needle to enter the sheath between the trap door and second side wall 26. Once the needle passes into the sheath past the trap door, the trap door resiliently returns towards second side wall 26 with the free end of the trap door adjacent door stop 28. Thereafter, during any attempt to cause the needle to exit the sheath the needle contacts the inner surface of the trap door. As a result, the trap door free end abuts door stop 28 to prevent the door from opening and, hence, the needle from leaving the sheath. Given the shape of the trap door and its connection at door hinge 24 to first side wall 22, the needle is trapped and prevented from leaving the sheath. Further pressure of the needle against the trap door causes the needle to slide down the inner surface of the trap door toward hinge 14, a closed area where the needle remains trapped. Alternatively, if the needle engages second side wall 26, the needle does not urged the trap door open.

Figure 3:
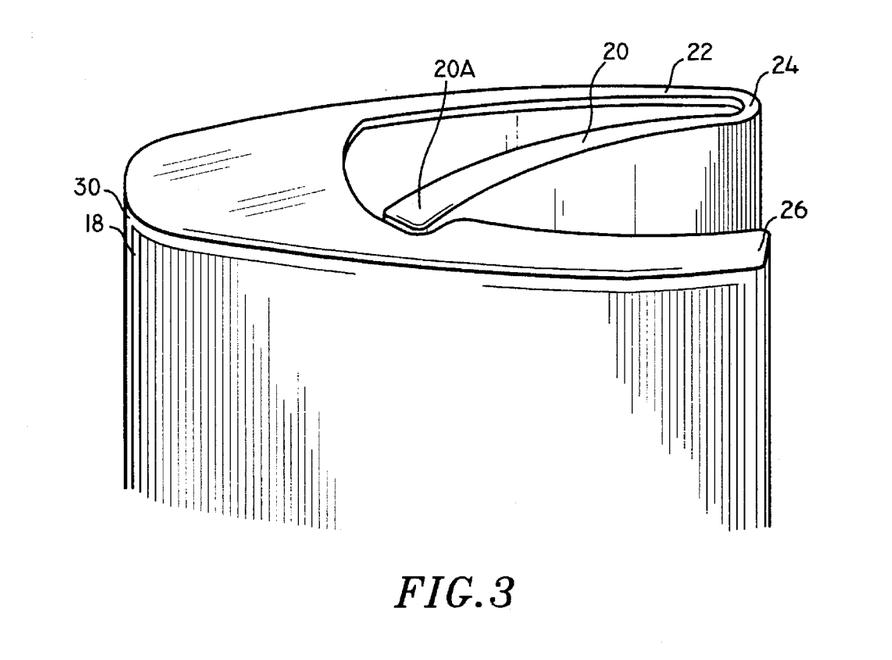
FIG. 3 is a partial perspective view of the distal end of the sheath of FIG. 1.

Referring to FIGS. 2 and 3, the proximal end of sheath 12 has a rear wall portion 30 connected to hinge 14, a first side wall 22 extending from the rear wall portion to flexible resilient trap door hinge 24, and a second wall portion 26 extending from the rear wall portion opposite the first wall portion. Trap door 20 is resiliently attached to first side wall 22 by flexible trap door hinge 24 and extends from door hinge 24 toward second wall portion 26. As shown, rear wall portion 30 and first side wall portion 22 may be of substantially uniform thickness. Second wall portion 26 may be of the same thickness as rear wall portion 30 and first side wall 22 over most of its length, but preferably includes a protruding area of increased rigidity adjacent door stop 28 to increase resistance to bending. As shown, hinge 24 is of reduced thickness to define a flexible resilient "living" trap door hinge. The living hinge biases trap door 20 toward second wall 26. As shown, the thickness of first side wall 22 may gradually decrease adjacent hinge 24, and trap door 20 preferably increases in thickness away from hinge 24 to provide rigidity to the housing other than in the area of hinge 14. It is alternatively contemplated that the thickness of side wall 22 may be substantially uniform and may change to a narrow thickness appropriate for hinge 14 immediately adjacent the hinge. Further, it is contemplated that rigidity may be imparted to desired areas by other known techniques, some of which may be preferable for molding consistency, such as providing lateral and/or horizontal reinforcing ribs in areas to be made more rigid and not providing such reinforcing ribs in areas to remain flexible.

FIG. 3 is a partial perspective view of the distal end of the housing. As shown, the housing preferably has a substantially closed distal end with open areas between first side wall 22 and trap door 20, and between trap door 20 and second side wall 26. The substantially closed distal end is preferred in order to further prevent contact with the tip of a needle disposed in the sheath. Providing open areas in the distal end adjacent the trap door, trap door hinge 24 and adjacent side walls 22 and 26 facilitates molding by providing access to these components from inside and outside the sheath in opposing directions, and by eliminating any need to mold a distal closed end extending over the trap door distal end. Although less preferred, it is contemplated that the distal end of the housing could be substantially open. Alternatively, it further is contemplated that the sheath could be tapered so that the rear sheath wall approaches the trap door to eliminate any need for a closed flat housing end wall.

One skilled in molding will understand that the sheath constructed as described herein is well suited for inexpensive molding. In particular, molding may be accomplished using a two part mold, with one part extending through the interior portion of the housing and the second part surrounding the housing exterior, eliminating any need for more complicated molds used to make the housing of Landis U.S. Pat. No. 4,664,259 and the Concord/Portex NEEDLE PRO devices.

Figure 4:
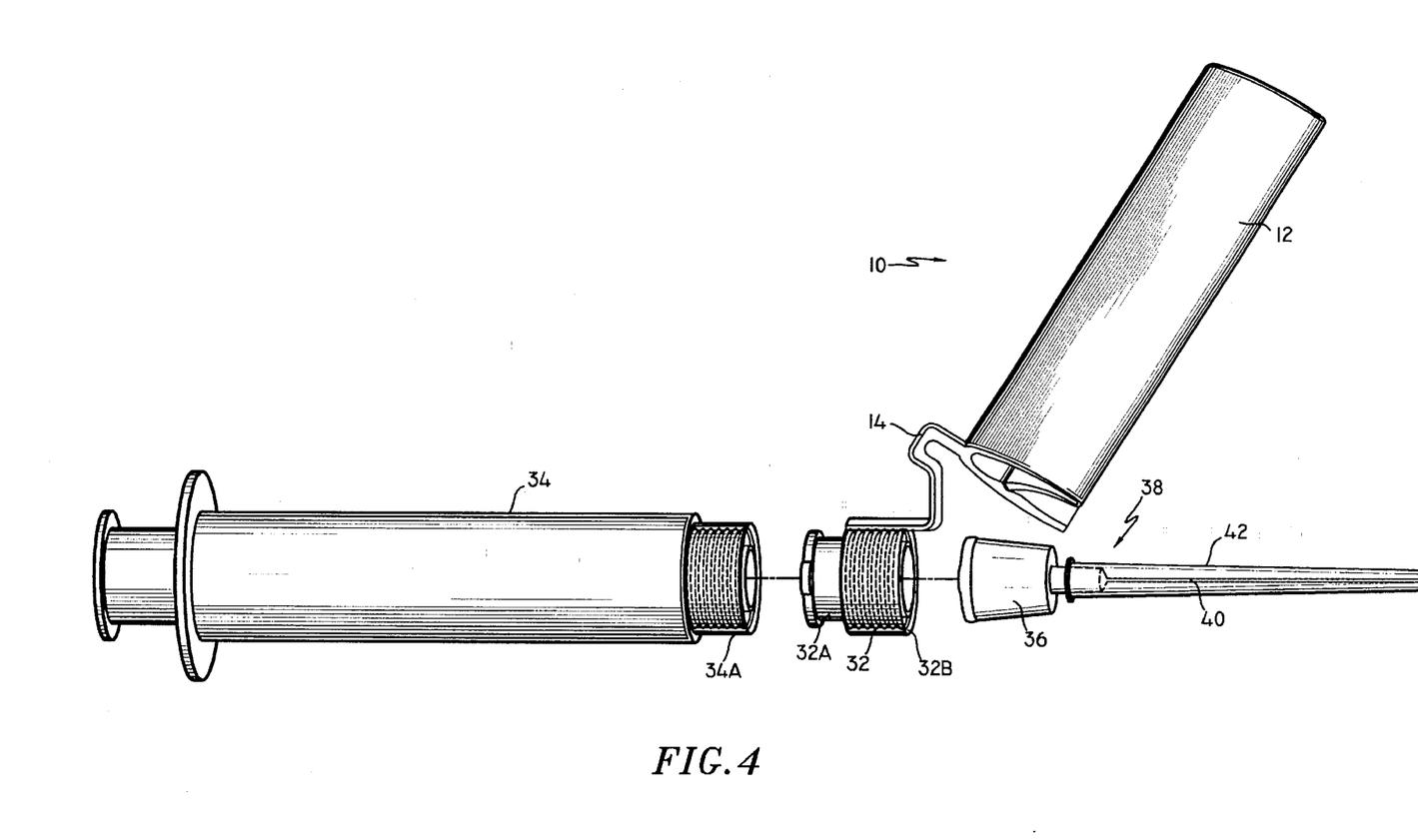
FIG. 4 is an exploded perspective view of the sheath of FIG. 1 attached to a luer fitting base, with a syringe, the luer base and sheath and a needle aligned longitudinally as they would be assembled.

FIG. 4 illustrates one contemplated mode of associating the safety sheath device 10 with the base of a needle. As described above, housing 12 is attached to hinge 14, preferably by molding the housing and hinge together as a single integral unit. In the mode of attachment shown in FIG. 4, the opposite end of hinge 14 away from housing 12 is attached to a luer type fitting 32. Hinge 14 preferably is molded together with fitting 32, so that fitting 32, hinge 14 and housing 12 may be formed as a single integrally molded unit. To facilitate molding, housing 12 and luer fitting 32 preferably are molded parallel to one another connected by hinge 14 and most preferably the hinge is molded to bias the sheath away from the luer fitting. Those skilled in molding will appreciate this configuration greatly simplifies molding operations. As shown in FIG. 4, fitting 32 has a male fitting 32a away from housing 12, a female receptor 32b toward housing 12 and a central axial aperture extending through the fitting. Male fitting 32a is configured and dimensioned to be threadingly attached to a syringe 34 at a female luer type fitting 34a such that the open end of the syringe communicates with the central axial aperture of fitting 32. Female receptor 32b of fitting 32 is configured and dimensioned to threadingly receive the base of a needle assembly 38. Needle assembly 38 is constructed in a known manner with needle 40 attached to needle base 36, such as by friction fit, either alone or in combination with medical grade adhesive, ultrasonic welding or the like. Needle 40 is a cannula type needle having a central axial chamber extending therethrough from the hollow needle base 36 to the open, sharp tip of the needle to convey medical solutions in a known manner. As shown in FIG. 4, needle assembly 38 typically also includes a cover sheath 42 to cover the needle prior to use.

To use the safety sheath device as shown in FIG. 4, the safety sheath device is attached to syringe 34 by engaging male luer fitting 32a with female receptor 34a of syringe 34 until a tight fit is obtained. With the safety sheath housing in an open position needle base 36 is mounted to luer fitting 32 as if the needle were being mounted directly to the syringe in the usual manner. Thus, the needle base 36 is tightly attached to syringe 34 and fluid communication is established between syringe 34 and needle 40 through the central aperture of luer fitting 32 which communicates with both syringe 34 and hollow needle base 36. It is also contemplated that the needle base 36 first could be attached to luer fitting 32 and that the combined safety sheath device and needle could thereafter be attached to syringe 34 as a combined unit.

After the assembly of the syringe, safety sheath housing and needle assembly is complete, the syringe and needle are used in a customary manner with the housing biased away from the needle. Cover sheath 42 is removed to expose needle 40, an appropriate medical solution is drawn into the syringe through the needle and luer fittings, and the injection is administered to a human or animal patient. Thereafter, the housing is rotated about hinge 14 with sufficient force to overcome the bias of hinge 14 and move the housing toward needle 40 to enclose the needle. The manner of engagement of housing 12 with needle 40 will be discussed below, particularly with reference to FIGS. 7A–7E, 8, 10A–10B and 11–12.

Figure 5:
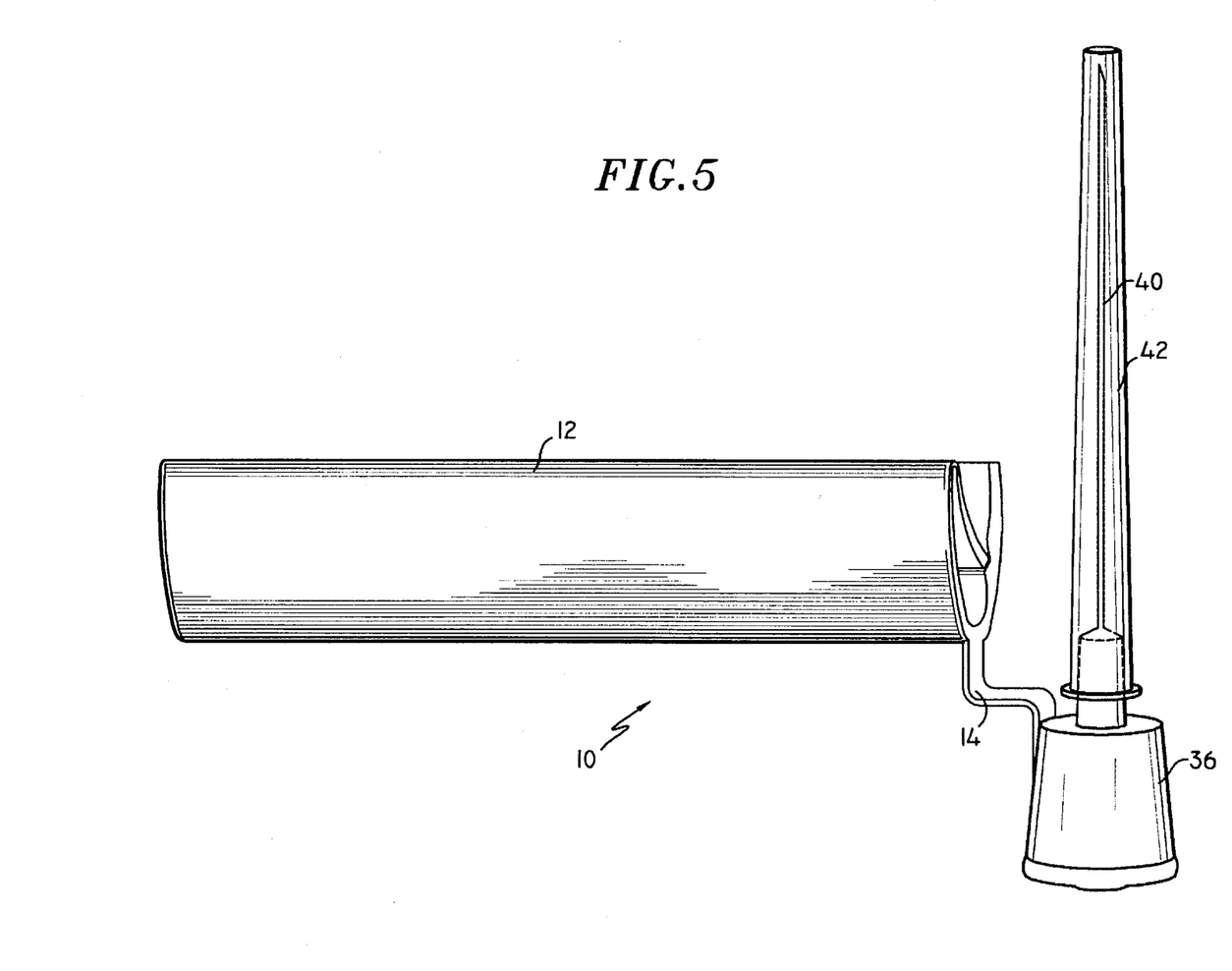
FIG. 5 is a partial perspective view of the sheath of FIG. 1 attached to a needle hub.
Figure 6:
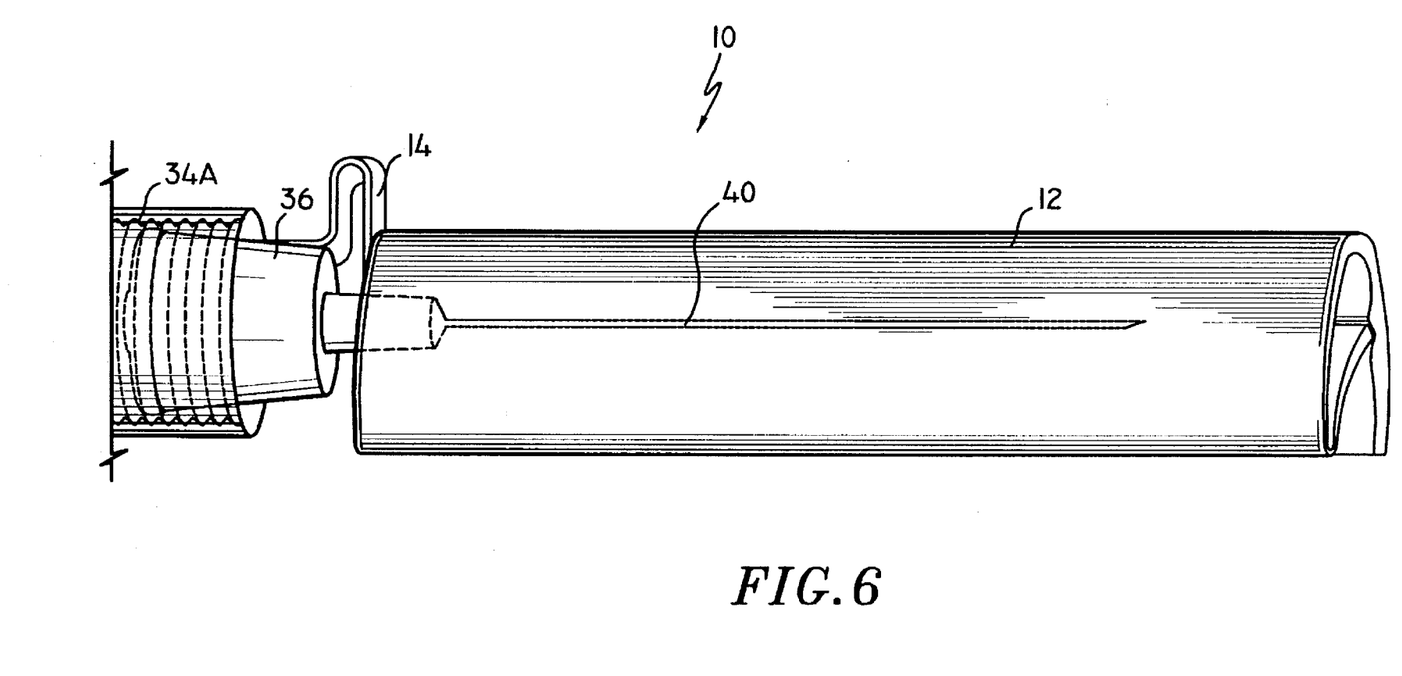
FIG. 6 is a partial perspective view of the sheath of FIG. 5 attached to the luer fitting of a syringe and closed about the needle after use.

Referring now to FIGS. 5 and 6, an alternative mode of associating safety sheath device 10 with the base of a surgical needle is shown. In FIG. 5 housing 12 is attached to hinge 14 which, in turn, is attached at the opposite end thereof away from housing 12 to needle base 36. In this embodiment, as in the embodiment of FIG. 4, housing 12 and needle base 36 are in an open orientation during molding. Needle 40 may thereafter be affixed to base 36 in any suitable manner, such as friction fit, adhesive attachment, ultrasonic welding or a combination thereof. A cover sheath 42 may also be provided to cover and protect the needle and user prior to use. Advantages of the alternative mode of attachment shown in FIG. 5 are that a safety sheath device can be provided with every needle and an intermediate step of attaching a luer fitting between the needle base and syringe is eliminated. As shown in FIG. 6, needle base 36 may be attached directly to syringe female luer receptor 34a in the usual manner without any intervening luer fitting 32 as shown in FIG. 4.

FIG. 6 illustrates the safety sheath device 10 of FIG. 5 in the closed condition covering needle 40 after use, i.e., after needle base 36 has been attached to a syringe, cover sheath 42 has been removed, a medical solution introduced into the syringe and injected into a patient, the needle has been removed from the patient and the housing has been rotated about housing hinge 14 into alignment with the needle.

While two methods of associating hinge 14 with the base end of a surgical sharp, e.g., a surgical needle, have been described, numerous alternative modes of associating the housing with a surgical sharp or needle to be covered will occur to those of ordinary skill in the art. By way of example only, luer fitting 32 could be adapted to receive a different size or type of needle, such as a double-ended needle typically used in blood sampling procedures. Alternatively, hinge 14 could be molded directly to the base of such a double-ended needle or to the container associated with the double-ended needle during blood sampling, known as a vacutainer. It is further contemplated that hinge 14 could be molded directly to a syringe which receives a needle, or to any other device which receives a surgical sharp or needle to be covered after use.

Figure 7A:
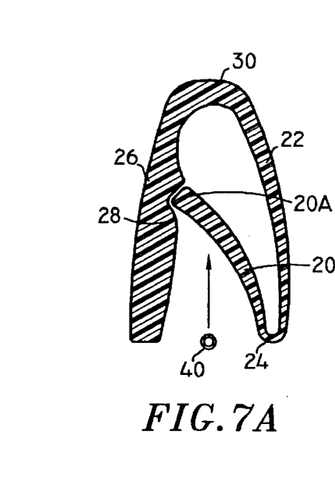
FIGS. 7A–7E are schematic cross-section views of the sheath of FIGS. 1–6 illustrating entry of a needle into the sheath.
Figure 7B:
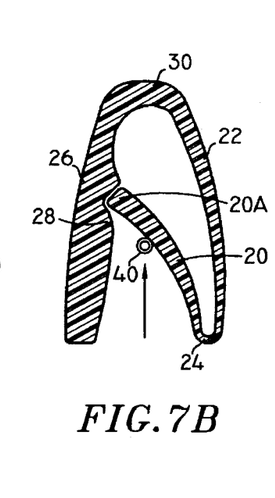
Figure 7C:
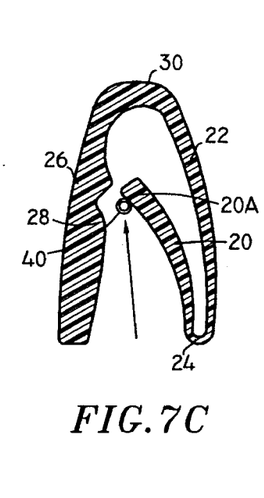
Figure 7D:
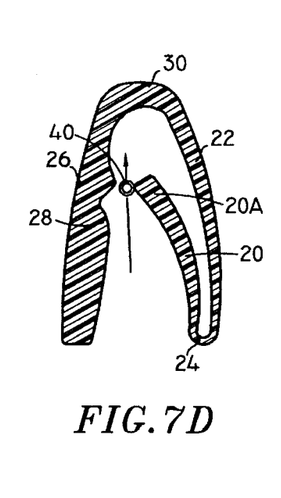
Figure 7E:
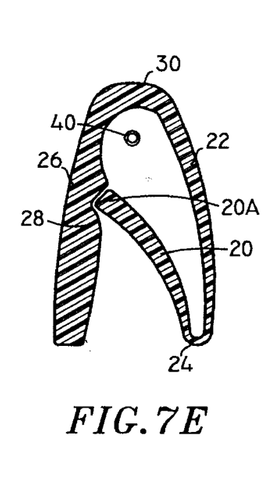

FIGS. 7A–7E are schematic illustrations of needle 40 passing through trap door 20 into sheath 12 as the sheath is rotated about hinge 14 into alignment with and enclosing the needle. In FIG. 7A needle 40 approaches but has not yet contacted trap door 20, which extends across the sheath entrance opening between hinge 24 and second side wall 26. In FIG. 7B needle 40 contacts trap door 20 but has not begun to flex the trap door about door hinge 24. In FIG. 7C, continued pressure of needle 40 against trap door 20 causes trap door 20 to flex toward side wall 22 about resilient door hinge 24. In FIG. 7D the needle begins to pass trap door end 20A, and in FIG. 7E needle 40 has entered the sheath and trap door 20 has resiliently returned under the influence of living hinge 24 to its original position to close the entrance of the sheath and prevent the needle from exiting the sheath. As best shown in FIGS. 7A–7E, the housing entrance is tapered and urges a needle entering the housing toward trap door free end 20A.

Figure 8:
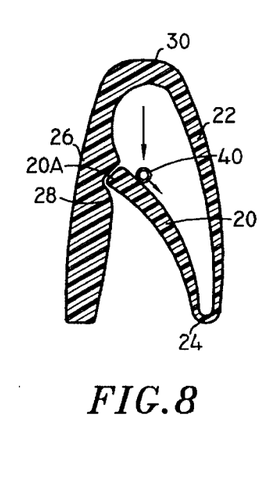
FIG. 8 is a schematic cross-section view of the action of the needle within the sheath during an attempt to re-open the sheath.

FIG. 8 is a schematic illustration of the forces at work to restrain the needle within the sheath during an attempt to open the sheath after the needle has entered the sheath. As shown, during any such attempt needle 40 contacts the inner surface of trap door 20. As shown, upon contacting the trap door the force of the needle against the trap door consists of a force vector substantially perpendicular to the inner door surface and a force vector substantially parallel to the inner trap door surface. The vector perpendicular to the trap door inner surface urges trap door free end 20A to abut door stop 28, which, in turn, prevents the trap door from pivoting away from first side wall 22. The force vector parallel to the inner trap door surface causes the needle to travel along the inner door surface toward resilient hinge 24. Thus, the force of the needle against the trap door causes the trap door to lodge against the door stop, which prevents the trap door from opening to allow the needle to exit the sheath. The force of the needle against the trap door also urges the needle into the enclosed space adjacent hinge 24 from which there is no exit. Of course, the particular forces and their direction to trap the needle will vary depending upon the particular housing, hinge and door configuration. In this manner, the needle is trapped within the sheath and prevented from exiting the sheath. In addition, the door closes the opening through which the needle entered the sheath to prevent particles or droplets from exiting the sheath toward the user.

Figure 9A:
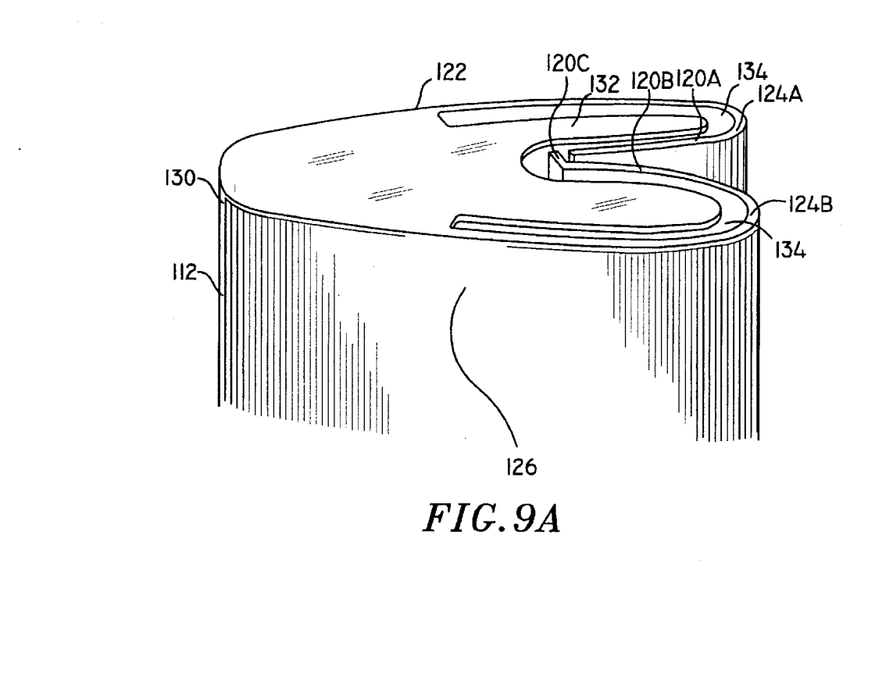
FIG. 9A is a partial perspective view of the distal end of a sheath constructed in accordance with an alternative embodiment.
Figure 9B:
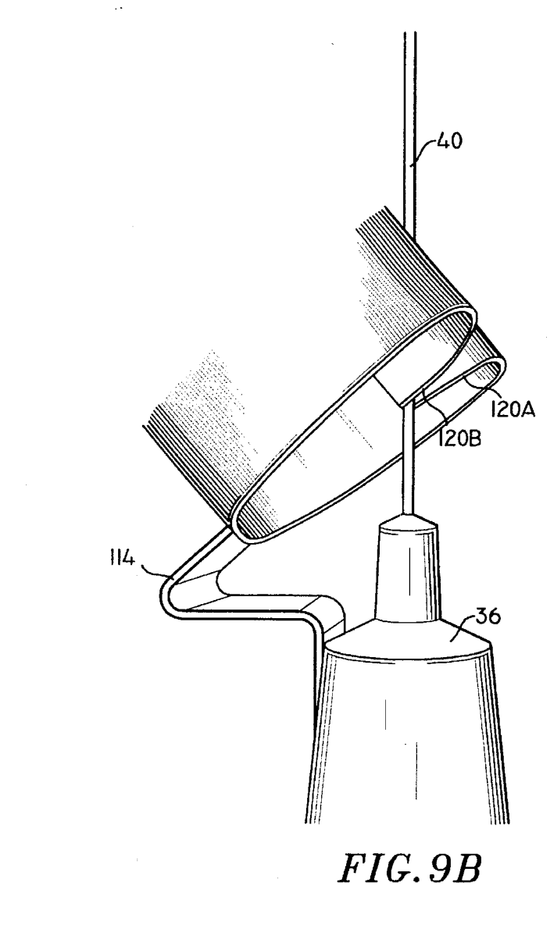
FIG. 9B is a partial perspective view of the proximal end of the sheath of FIG. 9A illustrating a needle entering the sheath as the sheath is rotated into alignment with the needle.

FIGS. 9A and 9B are perspective views illustrating an alternative embodiment of the sheath having a pair of trap doors extending across the sheath opening. In this embodiment, the housing includes a rear wall portion 130, a first side wall 122, a second side wall 126, and a closed housing distal end 132 (FIG. 9A). First side wall 122 is molded with an integral resilient hinge 124A and a first trap door 120A extending inwardly across a portion of the central entrance section of the housing. Second side wall 126 is molded with an integral resilient hinge 124B and a second trap door 120B also extending inwardly across the central entrance portion of the housing. Preferably, trap door 120B includes a stop section 120C overlapping and receiving the free end of first trap door 120A. Trap doors 120A, 120B extend the longitudinal length of the housing. Closed top or distal end 132 preferably terminates adjacent the entrance portion of the housing opposite rear wall 130, defining a gap 134 adjacent doors 120A, 120B. Gap 134 facilitates opening and closing of doors 120A, 120B and facilitates molding of the housing.

In use, the housing of the embodiment of FIGS. 9A and 9B is mounted to a surgical sharp in any suitable manner, such as the luer fitting of FIG. 4, mounting of the housing to a needle hub as in FIGS. 5–6, or any other suitable method of hingedly associating the housing with the surgical sharp. FIG. 9B is a partial perspective view of housing 112 hingedly connected to needle base 36 by housing hinge 114, illustrating the needle entering the housing through trap doors 120A, 120B. After the needle has been used, the housing is rotated about housing hinge 114 into alignment with the needle. The needle enters the housing between trap doors 120A, 120B, causing one or both of the doors to flex about resilient door hinges 124A, 124B. After the needle enters the housing past doors 120A, 120B, the trap doors resiliently return to the closed position shown in FIG. 9A. Thereafter, during any attempt to re-open the housing by rotating the housing out of alignment with the needle the needle will contact one or both trap doors. Because the trap doors abut each other and, preferably, overlap, the doors remain in the closed position and the needle cannot exit the housing. Indeed, continued force applied to rotate the housing out of alignment with the needle will likely result in the needle traveling along the inside surface of one of the doors to become trapped in the space adjacent one of resilient door hinges 124A, 124B.

The embodiments described above contemplate that the door member (FIGS. 1–8) or door members (FIGS. 9A and 9B) are configured and dimensioned not only to close the entrance portion of the housing but also to trap the needle within the housing and prevent the needle from leaving the housing. While it is preferred that the door member constitute both a trap door and a closure for the housing entrance, it is contemplated that the door member could be incorporated into a housing for only one of these purposes, or as a supplemental needle restraint but primarily as a closure for the entrance portion. Thus, where the door member is to perform only the function of securing the needle within the housing without regard for fully covering the needle entrance portion of the housing, a trap door extending less than the entire length of the housing entrance opening may be used, or two or more trap doors may be provided at different positions along the entrance opening.

It further is contemplated that the door member may be provided primarily for the purpose of preventing droplets or particles from exiting the housing. Thus, it is contemplated that the door member may be incorporated into a housing which also includes at least one needle-engaging hook member, such as the hook member shown in Landis U.S. Pat. No. 4,664,259 and incorporated into the Concord/Portex NEEDLE PRO devices.

Figure 10A:
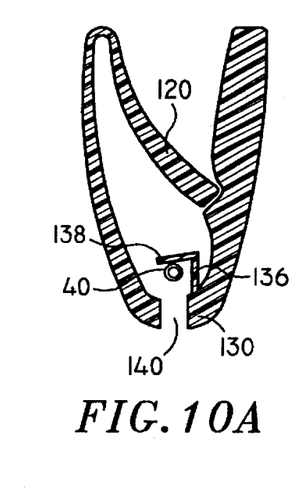
FIGS. 10A and 10B are cross-section views of an alternative sheath embodiment including a needle engaging hook member.
Figure 10B:
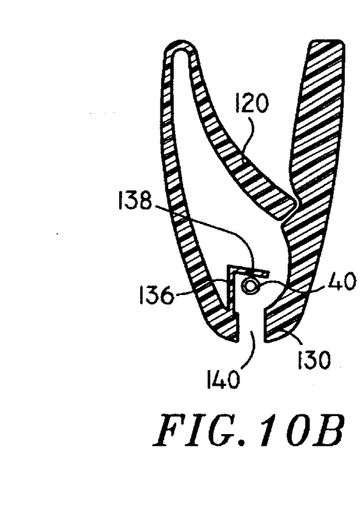
Figure 11:
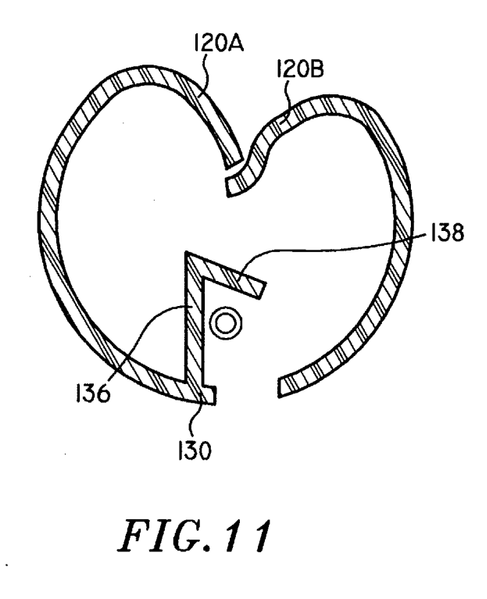
FIG. 11 is a cross-section view of an alternate sheath embodiment including a needle engaging hook member.
Figure 12:
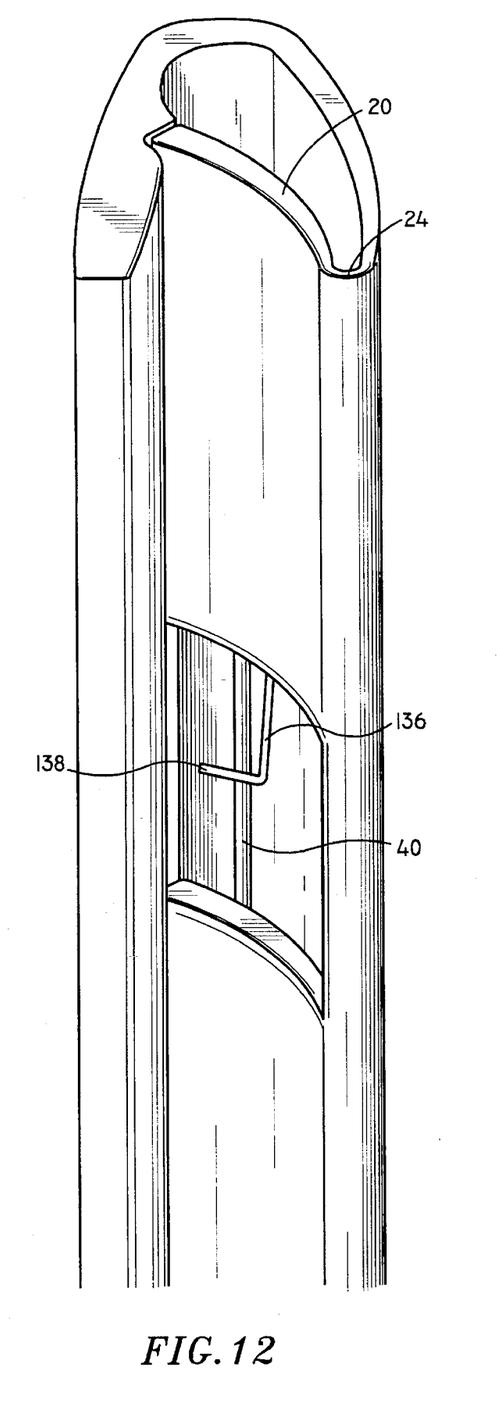
FIG. 12 is a partial perspective view of the embodiment of FIGS. 10A–10B illustrating a discontinuous door adjacent the needle engaging hook member.

FIGS. 10A–10B and 11 are cross-section views through a housing similar to those shown in FIGS. 1–9 but further including a needle engaging hook molded into the housing. Thus, it is contemplated that the device could include a needle-engaging hook 136 extending from rear wall 130. Hook 136 includes a tip 138 which traps the needle after entry into the housing through trap door 120. In the embodiments of FIGS. 10A and 10B, the needle enters the housing through trap door 120. In the embodiment of FIG. 11, the needle enters the housing through doors 120A, 120B. Thereafter, the needle passes hook tip 138 and snaps behind the hook tip by the resilient action of the hook and needle, similar to the manner in which the hook member of Landis U.S. Pat. No. 4,664,259 and the Concord/Portex NEEDLE PRO devices operate to secure the needle with a hook. In this manner the needle is securely trapped in the housing by the hook. The doors may provide added security to retain the needle in the housing, or may simply act as a barrier to substantially reduce if not eliminate the likelihood that particulate or droplet matter will be propelled out of the housing toward the user, particularly during or as a result of the snap action of the needle and hook member. As shown in the cross-section views of FIGS. 10A–10B and 11 and in the perspective view of FIG. 12 (corresponding to the embodiment of FIG. 11), it is contemplated that it may be necessary or desirable to make the door or doors discontinuous along the length of the housing to allow molding access for formation of the hook member. Similarly, it is contemplated that in the embodiments of FIGS. 10A–10B and 11 it may be necessary to provide a molding access hole 140 through rear wall 130 to facilitate molding hook member 136. The door(s) may extend substantially the entire length of the housing except where a gap is required to form the needle engaging hook member, or may extend adjacent only a portion of the needle entrance opening adjacent the hook, particularly in the area of the housing occupied by the tip of the needle. Thus, in the embodiments of FIGS. 10A–10B and 11–12 the door may be included in the housing only to prevent droplets or particles from exiting the housing. Under these circumstances the door need not be sufficiently rigid to prevent the needle from exiting the housing. Alternatively, the door may be sufficiently rigid to prevent the needle from leaving the housing as well as preventing droplet or particulate matter from leaving the housing, with the hook provided for added security.

As in the case of the embodiments shown in FIGS. 1–9, the housings of FIGS. 10A–10B and 11–12 are mounted by a housing hinge adjacent the base of a surgical sharp such as a cannula type needle. The housing hinge biases the housing away from the needle. After use of the needle, the housing is rotated about the hinge into alignment with the needle, so that the needle enters the housing through the door(s) and engages the hook member to retain the needle within the housing and prevent droplets or particles from exiting the housing through the entrance aperture toward the user.

The foregoing description contains many specifics, but one skilled in the art will understand and appreciate from the disclosure contained herein and from experience and experimentation with the device that numerous variations, modifications and improvements may be made to the device within the spirit of the invention and the scope of the appended claims.

What is claimed is:

1. In a needle protection device having an elongated housing pivotal to enclose a needle, the housing including a longitudinal slot for receiving a needle therethrough as the housing is pivoted to enclose the needle, the improvement comprising at least one elongated door member hingedly attached to the housing and extending across the longitudinal slot over substantially the entire length of the longitudinal slot, the door member being biased to close the longitudinal slot after a needle has entered the housing through the longitudinal slot.

2. The needle protection device of claim 1 wherein the elongate door member comprises a trap door extending from a first side wall of the housing to a second side wall of the housing, the trap door abutting a door stop on the second side wall.

3. The needle protection device of claim 1 wherein the at least one elongate door member comprises a pair of elongate doors each extending from a side wall of the housing, the doors overlapping to close the housing.

4. The needle protection device of claim 1 wherein the elongate door member is attached to the housing by a resilient living hinge.

5. A surgical sharp protection device comprising:
   an elongate housing having a first end hingedly associated with the base of a surgical sharp, the housing having a rear wall portion, first and second side wall portions defining an elongate surgical sharp entrance slot therebetween extending away from the base of the surgical sharp, and at least one door member hingedly attached to at least one side wall and extending across substantially the entire length of the entrance slot.

6. The device of claim 5 wherein the at least one door member comprises a trap door attached by a resilient door hinge member to the first side wall and extending adjacent the second side wall.

7. The device of claim 6 wherein the resilient door hinge is a living hinge.

8. The device of claim 6 wherein the housing, trap door and resilient hinge are integrally molded.

9. The device of claim 6 wherein the second side wall includes a door stop.

10. The device of claim 9 wherein the trap door is rotatable about the door hinge toward the first side wall, the door stop limiting rotation of the door about the door hinge away from the first side wall.

11. The device of claim 5 wherein the surgical sharp is a surgical needle.

12. The device of claim 5 wherein the housing further includes a needle engaging hook member.

13. The device of claim 5 wherein the at least one door member comprises a pair of doors, each door hingedly attached by a resilient door hinge to one of the side walls.

14. In combination:

a surgical needle attached to a needle base;

an elongated housing having a first proximal end adapted to be hingedly associated with the needle base, the elongate housing extending distally away from the needle base and having side walls defining an elongate entrance slot to receive the needle therethrough as the housing is pivoted relative to the needle base, the housing including at least one door member extending across at least the distal portion of the entrance slot adjacent the needle tip.

15. The combination of claim 14 wherein the housing is hingedly rotatable into alignment with the needle, the needle entering the housing through the elongate entrance slot past the door member.

16. The combination of claim 14 wherein the at least one door member comprises a trap door attached by a resilient door hinge member to the first side wall and extending adjacent the second side wall.

17. The combination of claim 16 wherein the resilient door hinge is a living hinge.

18. The combination of claim 16 wherein housing, trap door and resilient hinge are integrally molded.

19. The combination of claim 16 wherein the second side wall includes a door stop.

20. The combination of claim 19 wherein the trap door is rotatable about the door hinge toward the first side wall, the door stop limiting rotation of the door about the door hinge away from the first side wall.

21. The combination of claim 20 wherein the needle enters the housing through the door as the housing is rotated into alignment with the needle, the needle contacting the door and urging the door toward the first side wall about the door hinge, the door being biased toward contact with the door stop to thereafter prevent the needle from leaving the housing after the needle has entered the housing through the slot and the door is biased toward the door stop.

22. The combination of claim 14 wherein the housing further includes a needle engaging hook member.

23. The combination of claim 14 wherein the at least one door member comprises a pair of doors, each door hingedly attached by a resilient door hinge to one of the side walls.

24. The combination of claim 14 wherein the elongate housing is hingedly attached to a luer fitting engagable with a needle hub.

25. The combination of claim 14 wherein the elongate housing is hingedly attached to a needle hub.

26. The combination of claim 14 wherein the elongate housing is hingedly attached to a syringe.

27. The combination of claim 14 wherein the elongate housing is hingedly attached to a vacutainer.

28. The combination of claim 14 wherein the elongate entrance portion is tapered to urge the needle toward the center of the housing.

29. A method of reducing the likelihood of contact with a needle or matter thereon, comprising:

providing a needle protection device having an elongated housing pivotal to enclose a needle, the housing including a longitudinal slot to receive the needle therethrough and at least one elongate door member extending over substantially the entire length of the slot hingedly attached to the housing and biased to close the slot;

rotating the housing into alignment with the needle so that the needle enters the housing through the longitudinal slot past the door member, the door member resiliently closing the slot to contain the needle within the housing after the needle has passed the door member.

30. A method of reducing the likelihood of contact with a needle or matter thereon, comprising:

providing a surgical needle attached to a needle base with an elongate housing having a first end adapted to be hingedly associated with the needle base, the elongate housing extending distally away from the needle base and having first and second side walls defining an elongate needle entrance slot, the housing including at least one door member hingedly attached to the first side wall and extending across at least a portion of the entrance slot;

rotating the housing into alignment with the needle so that the needle enters the housing through the entrance slot past the door member, the door member resiliently closing at least the distal portion of the entrance slot to enclose at least the tip portion of the needle.

* * * * *